US005468866A

United States Patent [19]
Highsmith et al.

[11] Patent Number: 5,468,866
[45] Date of Patent: Nov. 21, 1995

[54] METHODS FOR SYNTHESIZING AND PROCESSING BIS-(1(2)H-TETRAZOL-5-YL)-AMINE

[75] Inventors: Thomas K. Highsmith, North Ogden; Robert M. Hajik, Willard; Robert B. Wardle, Logan; Gary K. Lund, Ogden; Reed J. Blau, Richmond, all of Utah

[73] Assignee: Thiokol Corporation, Ogden, Utah

[21] Appl. No.: 177,737

[22] Filed: Jan. 4, 1994

[51] Int. Cl.$^6$ ................................................ C07D 403/12
[52] U.S. Cl. .............................................. 548/251; 548/250
[58] Field of Search ........................................... 548/251

[56] References Cited

U.S. PATENT DOCUMENTS

| | | | |
|---|---|---|---|
| 3,468,730 | 9/1969 | Gawlick et al. | 149/61 |
| 3,719,604 | 3/1973 | Prior et al. | 252/186 |
| 3,739,574 | 6/1973 | Godfrey | 60/39.03 |
| 3,778,084 | 12/1973 | Sutherland et al. | 280/150 AB |
| 3,898,112 | 8/1975 | Strecker et al. | 149/19.9 |
| 4,142,029 | 2/1979 | Illy | 521/95 |
| 4,608,102 | 8/1986 | Krampen et al. | 149/92 |
| 4,909,549 | 3/1990 | Poole et al. | 280/738 |
| 4,948,439 | 8/1990 | Poole et al. | 149/46 |
| 5,035,757 | 7/1991 | Poole | 149/46 |
| 5,084,118 | 1/1992 | Poole | 149/22 |
| 5,139,588 | 8/1992 | Poole | 149/61 |
| 5,197,758 | 3/1993 | Lund et al. | 280/741 |

FOREIGN PATENT DOCUMENTS

0519485A1  12/1992  European Pat. Off. .......... C06D 5/60

OTHER PUBLICATIONS

The Merck Index Rahway, N. J., (4), 1983 p. 1323, compound No. 1320.
G. C. Chiang, "Preparation of 2–aminotriazine herbicide intermediates via metal dicyanimide ligand complexes," *Chemical Abstracts*, vol. 113, No. 231414f, p. 728, 1990.
Nakamura, et al., "Preparation of calcium dicyanamide aqueous solution as a pharmaceutical starting material," *Chemical Abstracts*, vol. 109, No. 148873b, p. 671, 1988.
Nakamura, et al., "A process for the preparation of dicyanamide metal salts as intermediates for antimicrobials," *Chemical Abstracts*, vol. 109, No. 210568m, p. 618, 1988.
W. P. Norris and R. A. Henry, "Cyanoguanyl Azide Chemistry," pp. 650–660, Mar. 1964.
M. Kuhn and R. Mecke, "IR–Spektroskopische Untersuchungen am Dicyanamid–Anion," *Chem. Ber.*, vol. 94, pp. 3010–3015, 1961.
Joseph S. Mihina, et al., "The Reaction of Nitriles With Hydrazioc Acid: Synthesis of Monosubstituted Tetrazoles," Kedzie Chemical Lab., pp. 1082–1092, Apr. 1950.
R. Stollé, "5–Aminotetrazole," *Chemical Abstracts*, *10–Organic Chemistry*, vol. 23, p. 4471, 1929.
R. Stollé et al., "Zur Kenntnis des Amino–5–tetrazols," *Chem. Ber.*, vol. 62, pp. 1118–1127, 1929.
William L. Burdick, "Some Ammono–Carbonic Acids and Their Reactions in Liquid Ammonia," *The Journal of the American Chemical Society*, vol. 47, No. 6, pp. 1485–1491, Jun. 1925.
R. N. Butler, "Tetrazoles," *Comprehensive Heterocyclic Chem.*, pp. Chpt. 4.13, 791–838 (no date found).

Primary Examiner—David B. Springer
Attorney, Agent, or Firm—Ronald L. Lyons; Madson & Metcalf

[57] ABSTRACT

Methods of preparing bis-(1(2)H-tetrazol-5-yl)-amine (BTA) having improved physical and chemical characteristics are disclosed. In the process, a dicyanamide salt and an azide salt are reacted at high temperature in the presence of an acid reagent. Best yields are obtained when the reaction is allowed to proceed for approximately 48 hours. The dicyanamide salt is preferably present in a stoichiometric excess. The acid reagent has a $pK_a$ in the range from about 3 to about 9. The reaction mixture is acidified to a pH less than 3. Several variations of the acidification step permit control of particle size and morphology. Small, rounded particles are prepared by rapidly cooling the hot crude reaction product coincidentally with acidification. This is preferably accomplished by adding the hot crude reaction product directly to cold concentrated acid. The precipitated particles are isolated to yield BTA.

43 Claims, 4 Drawing Sheets

METHODS FOR SYNTHESIZING AND PROCESSING BIS-(1(2)H-TETRAZOL-5-YL)-AMINE

FIELD OF THE INVENTION

The present invention relates to an improved method of synthesizing bis-(1(2)H-tetrazol-5-yl)-amine and to processing techniques which improve the physical and chemical characteristics of bis-(1(2)H-tetrazol-5-yl)-amine.

BACKGROUND OF INVENTION

A method of synthesizing bis-(1(2)H-tetrazol-5-yl)-amine is described by William P. Norris and Ronald A. Henry, "Cyanoguanyl Azide Chemistry," *Journal of the American Chemical Society*, pp. 650–660, March 1964, which is incorporated herein by reference. Bis-(1(2)H-tetrazol-5-yl)-amine (herein after referred to as BTA) has the following structure:

The BTA synthesis method described by Norris et al. reacts sodium dicyanamide (0.1 mole), sodium azide (0.22 mole), and trimethylammonium chloride catalyst (0.22 mole) in 100 ml of water at refluxing temperature for 23 hours.

The Norris et al. process has several significant disadvantages. For instance, the tertiary alkyl amine catalyst used by Norris et al., trimethylammonium hydrochloride, is not available on a large scale and is expensive. Furthermore, the tertiary alkyl amine is released during the reaction process, and it has a pungent, obnoxious odor. It will be appreciated that it would be an advancement in the art to provide a process of preparing BTA which uses a readily available, low cost catalyst which does not smell bad.

Another important disadvantage of the Norris et al. process is the use of excess sodium azide. Because excess sodium azide is used, sodium azide is present throughout the reaction process and is left over upon completion. This represents a safety and disposal concern. In addition, according to the reaction process of Norris et al., treatment of the final reaction mixture with acid results in the formation of hydrazoic acid ($HN_3$) which is a vasodilator and explosive. It would be a significant advancement in the art to provide a process of preparing BTA which avoids or minimizes the formation of hydrazoic acid.

Yet another disadvantage of the Norris et al. process is in purification of the final product. Norris et al. teaches that the hot reaction mixture is treated with concentrated hydrochloric acid and then cooled. This results in entrapment of the sodium salt within the particles. Since an important use of the final BTA product is as the primary fuel of a gas generant composition, particle purity is important. It is known that contaminants, including salts such as chloride and sodium salts, adversely affect burn rate. Accordingly, it would be an advancement in the art to provide a process of preparing BTA having a purity suitable for use in gas generant devices.

The Norris et al. process consistently produces large crystals. It has been found that this results from final acidification at high temperature. Small, rounded particles having a high surface area are often preferred in gas generant formulations. Thus, it would be an advancement in the art to provide a process of preparing BTA which produces small, rounded BTA particles.

Such processes for preparing BTA are disclosed and claimed herein.

SUMMARY OF THE INVENTION

The present invention is directed to a method of synthesizing bis-(1(2)H-tetrazol-5-yl)-amine ("BTA") and to processing techniques which improve the physical and chemical characteristics of BTA. The reaction for preparing BTA is shown below:

In the process according to the present invention, an azide salt, a dicyanamide salt, and an acid reagent are combined in water. At least one mole of the dicyanamide salt is present for every two moles of the azide salt and at least one mole (and preferably 1.5 mole) of the acid reagent is present for each mole of the azide salt. It has been found that the reaction proceeds best when the acid reagent has a $pK_a$ in the range from about 3 to about 9, and preferably from 3.5 to about 4.5. The acid reagent is preferably soluble at low pH and low temperature so that it remains in solution during acidification of the BTA. In addition, the acid reagent should not participate or interfere with the reaction. Suitable inorganic and organic acids may be used. Acid reagents which may be used in the present invention include boric acid, ammonium chloride, buffer systems based on phosphate or acetate, chloroacetic acid, formic acid, malic acid, malonic acid, glycolic acid, and lactic acid.

The reaction solution is heated to a temperature greater than 65° C. and preferably at reflux temperature. The reaction ingredients may be combined either prior to or during the heating step. After the reaction is substantially complete, the reaction solution is acidified and the final bis-(1(2)H-tetrazol- 5-yl)-amine product is isolated, preferably by filtering and washing with water.

Several variations of the acidification step are possible. For example, acid may be introduced into the reaction solution by direct addition or the reaction solution may be introduced into acid by indirect addition. The resulting particle size and morphology is controlled by the acidification step. For instance, if the reaction solution is warm during acidification, then the resultant particles are generally larger and more crystalline than particles formed during a rapid cooling acidification. It is generally preferred that acid and reaction solution be agitated during the acidification step. Generally, sufficient acid is used in the acidifying step to lower the reaction solution's pH to a value of 3 or below. Thus, the acid used to acidify the reaction solution preferably has a $pK_a<2$. The acid is also preferably soluble in the reaction solution at the pH range and temperature of the reaction. Inorganic and organic acids may be used in the acidification step. Currently preferred acids include HCl, $H_2SO_4$, $H_3PO_4$, $HNO_3$, $Cl_2CCO_2H$, $Cl_3CCO_2H$, $F_3CCO_2H$, $HCO_4$, and mixtures thereof.

DETAILED DESCRIPTION OF THE INVENTION

In the process of the present invention, a dicyanamide salt and an azide salt are reacted in the presence of an acid reagent. The reaction preferably takes place at a temperature in the range from about 65° C. to reflux temperature. After the reaction is substantially complete, the reaction solution is acidified to protonate the BTA, and the product is isolated, preferably by filtering and washing with water.

In contrast to prior art teachings, the dicyanamide salt is preferably present in a stoichiometric excess, that is, at least one mole of the dicyanamide salt is present for every two moles of azide salt. Two possible reasons for having a stoichiometric excess of the dicyanamide salt are because (1) the dicyanamide decomposes during the course of the reaction (estimated to be about 6% over 24 hours as shown in Example 19) and (2) the commercially available dicyanamide is of low purity (about 85%). In addition, it is important to minimize the amount of azide present during acidification to avoid or minimize hydrazoic acid production. Organic and inorganic salts of dicyanamide may be used. Typical salts include the Ag, Ca, Cd, Cs, Cu, Fe, K, Mg, Na, and Zn dicyanamide salts, and mixtures thereof. The alkali and alkaline earth dicyanamide salts are preferred with sodium dicyanamide being currently most preferred.

At least one mole, and preferably 1.5 mole, of the acid reagent is preferably present for each mole of the azide salt. The reaction proceeds best when the acid reagent has a $pK_a$ in the range from about 3 to about 9, and preferably from about 3.5 to about 4.5. The acid reagent is preferably soluble at low pH and low temperature so that it remains in solution during acidification of the BTA. In addition, the acid reagent should not participate or interfere with the reaction, that is, it does not react with the azide salt or dicyanamide salt under the reaction conditions. Suitable inorganic and organic acids may be used. Acid reagents which may be used in the present invention include boric acid, ammonium chloride, buffer systems based on phosphate or acetate, chloroacetic acid, formic acid, malic acid, malonic acid, glycolic acid, and lactic acid.

The reaction solution is heated to a temperature greater than 65° C., and preferably at reflux temperature. The reflux temperature will vary depending on the ingredient concentrations and upon the local elevation or barometric pressure. The reflux temperature will generally be greater than 95° C. It is possible to increase the reflux temperature by applying pressure to the reaction. It has been observed that yields improve as the reaction temperature approaches reflux; therefore, the reaction temperature is preferably at or near the reflux temperature (greater than about 95° C.). The reaction ingredients may be combined either prior to or during the heating step.

The relative crystallinity is determined by scanning electron micrographs (SEM). Particles having a greater "sparkly" appearance are more crystalline. The amorphous character of BTA can be maximized by rapidly cooling the crude product coincidentally with acidification. Thus, the resulting particle size and morphology is controlled by the acidification step. For example, if the reaction solution is warm during acidification, then the resultant particles are generally larger and more crystalline than particles formed during a rapid cooling acidification. It has been found that slow cooling results in the formation of long crystals and entrapment of salts, whereas rapid cooling produces smaller, rounded particles with little salt entrapped.

As illustrated in the examples, below, several variations of the acidification step are possible. Acid may be introduced into the reaction solution by direct addition or the reaction solution may be introduced into acid by indirect addition. In addition, the temperature of the reaction solution and acid may also vary. Further reduction in particle size is achieved by rapid agitation of the solutions. The reaction solution is preferably acidified to a pH less than 3 to ensure that the BTA is fully protonated. Taking the solution to a low pH also dramatically improves purity by reducing the presence of salt impurities. The acid used to acidify the reaction solution preferably has a $pK_a<2$. The acid is also preferably soluble in the reaction solution at the pH range and temperature of the reaction. Inorganic and organic acids may be used in the acidification step. Currently preferred acids include HCl, $H_2SO_4$, $H_3PO_4$, $HNO_3$, $Cl_2CCO_2H$, $Cl_3CCO_2H$, $F_3CCO_2H$, $HClO_4$, and mixtures thereof.

After acidification, the precipitated particles are isolated. Conventional particle separation techniques may be used such as centrifugation, filtration, and ultrafiltration, with filtration and washing being currently preferred. Washing removes acid and soluble by-products. Typically, the final product is washed with water until the effluent has a pH of about 2 to 3.

An important advantage of the present invention is the ability to obtain pure BTA suitable for its intended use without further purification. In contrast, the process of Norris et al. produces impure product which must be purified in subsequent purification steps. Further purification may be obtained using conventional techniques, such as recrystallization from methanol or ethanol.

The present invention is further described in the following nonlimiting examples.

EXAMPLE 1

In a 1 liter round bottom flask with magnetic stirrer and reflux condenser were combined 47 g of ammonium chloride, 37 g of sodium dicyanamide and 57.2 g of sodium azide. The resulting mixture was heated to reflux for 18 hours then diluted with 400 ml of hot water then acidified with a mixture of 200 ml water and 100 ml of concentrated hydrochloric acid. Upon completion of the acidification, no precipitate had formed in the hot solution. The reaction solution was cooled at 5° C. for 4 hours. The precipitate was isolated by filtration, washed with water, and dried in vacuum to afford 53.4 g of BTA. Based on $^{13}C$ NMR, the BTA was impure.

EXAMPLE 2

In a 500 ml round bottom flask with magnetic stirrer and reflux condenser were combined with 200 ml of water, 18 g sodium dicyanamide, 6.8 g potassium dihydrogenphosphate and 17.4 g of dipotassium hydrogenphosphate to obtain a pH of 7.0 upon equilibrium. To this solution were added 28.6 g of sodium azide and the resulting solution was heated to reflux for 72 hours. At this point, the pH was 11–12. Without cooling the solution, concentrated hydrochloric acid was added slowly until the pH was roughly 1. The solution was allowed to cool to room temperature. At approximately 60° C., precipitate formed. The reaction was diluted with 200 ml methanol and cooled at roughly 5° C. for 4 hours. The solid was isolated by filtration. By this method 8.5 g (20% yield based on dicyanamide) of BTA were obtained.

EXAMPLE 3

In a 500 ml round bottom flask with magnetic stirrer and reflux condenser were combined 300 ml of water, 18 g sodium dicyanamide, 13.6 g potassium dihydrogenphosphate and 17.4 g of dipotassium hydrogenphosphate to obtain a pH of 7.0 upon equilibrium. To this solution were added 28.6 g of sodium azide and the resulting solution was heated to reflux for 18 hours. At this point, the pH was 10.5. Without cooling the solution, concentrated hydrochloric acid was added slowly until the pH was roughly 1. The solution was allowed to cool to room temperature. The solid was isolated by filtration. By this method 14.4 g of BTA were obtained.

EXAMPLE 4

In a 1000 ml round bottom flask with magnetic stirrer and reflux condenser were combined 500 ml of water, 71.2 g sodium dicyanamide, 68.1 g potassium dihydrogenphosphate and 43.5 g of dipotassium hydrogenphosphate to obtain a pH of 7.0 upon equilibrium. To this solution were added 107.25 g of sodium azide and the resulting solution was heated to reflux for 30 hours. At this point, the pH was 11. While the solution was hot, concentrated hydrochloric acid was added slowly until the pH was roughly 3.5. Thus solution was allowed to cool to room temperature and the solid was isolated by filtration. The solid was recrystallized from water to afford 43 g of BTA.

Examples 5–7, below, illustrate a method of isolating and purifying the BTA in which no hydrazoic acid is produced. In the method, a soluble zinc salt, such as zinc acetate dihydrate, zinc nitrate, or zinc chloride, is added to the reaction solution before acidification. The zinc forms an insoluble precipitate with BTA which is isolated from any unreacted azide. The zinc BTA complex is then digested with strong acid at a temperature greater than 50° C. to remove zinc salts and to protonate the BTA. It will be appreciated that other cations besides zinc may be used, provided that the cation is soluble with $N_3^-$ and insoluble with BTA.

EXAMPLE 5

In a 500 ml round bottom flask with magnetic stirrer and reflux condenser were combined 200 ml of water, 18 g sodium dicyanamide, 39.3 g of potassium acetate and added acetic acid to obtain a pH of 7 upon equilibrium. To this solution were added 25 g of sodium azide and the resulting solution was heated to reflux for 2 hours. At this point, the pH was 11. The pH was adjusted to 7 by addition of acetic acid. Each 30 minutes for the next two hours, the pH was checked and then adjusted back to 7. After 24 hours, the pH was roughly 10.5 then adjusted to pH 7 with acetic acid. After cooling, the resulting solution was added to a solution of 44 g of zinc acetate dihydrate in 1000 ml of water. The solid was collected by filtration and washed with water. The solid was slurried in water, acidified to pH 0–1 with hydrochloric acid. The solid dissolved and then a precipitate slowly formed upon standing. The solid was isolated by filtration, washed with water, and vacuum dried. By this method 11 g of BTA were obtained.

EXAMPLE 6

In a 500 ml round bottom flask with magnetic stirrer and reflux condenser were combined 200 ml of water, 18 g sodium dicyanamide, 39.3 g of potassium acetate and added acetic acid to obtain a pH of 7. To this solution were added 27.3 g of sodium azide and the resulting solution was heated to reflux. At this point, acetic acid was added by syringe pump at the rate of 3 ml per minute for 4 hours. The pH was roughly 7. After 24 hours reflux, the pH was roughly 8. After cooling, the resulting solution was added to a solution of 44 g of zinc acetate dihydrate in 500 ml of water. The solid was collected by filtration and washed with 1350 ml water. The solid largely dissolved and then a precipitate slowly formed upon standing. The solid was isolated by filtration, washed with water and vacuum dried. By this method 11.5 g of BTA were obtained.

EXAMPLE 7

In a 500 ml round bottom flask with magnetic stirrer and reflux condenser were combined 200 ml of water, 18 g sodium dicyanamide, 39.3 g of potassium acetate and added acetic acid to obtain a pH of 7. To this solution were added 27.3 g of sodium azide and the resulting solution was heated to reflux. At this point, acetic acid was added by syringe pump at the rate of 3 ml per minute for 3 hours. The pH was roughly 7. The acetic acid addition rate was slowed to 0.6 ml per hour, and was added until 24 ml acetic acid were added. After 24 hours reflux, the solution was cooled to ambient. After standing for 24 hours, 600 ml of water were added and the resulting solution was added to a solution of 44 g of zinc acetate dihydrate in 500 ml of water. The solid was collected by filtration and washed with 1350 ml water. The solid was slurried in 400 ml water and acidified to pH 0–1 with 1–200 ml hydrochloric acid. The solid largely dissolved and then a precipitate slowly formed upon standing. The solid was isolated by filtration, washed with water and vacuum dried. By this method 23.5 g of BTA were obtained.

EXAMPLE 8

In a 2 liter round bottom flask with a magnetic stirrer and reflux condenser were combined 800 ml of water, 72 g of sodium dicyanamide, 169.6 g of dimethylammonium chloride, and 114.4 g of sodium azide. The resulting solution was refluxed for 48 hours then transferred to a 4 liter beaker. The solution was acidified with 200 ml of concentrated hydrochloric acid. The resulting slurry was allowed to cool to ambient temperature then cooled in an ice bath. The solid was isolated by filtration and air dried to afford roughly 200 g wet BTA. Based on $^{13}C$ NMR, the BTA product was impure.

EXAMPLE 9

In a 1 liter three-necked round bottom flask with an overhead stirrer, reflux condenser, addition funnel, thermometer and nitrogen inlet were combined 400 ml water, 47 g of ammonium chloride, 37 g of sodium dicyanamide and 57.2 g of sodium azide. The resulting solution was heated to 92°–95° C. for 24 hours then diluted with 200 ml water. Concentrated hydrochloric acid was added via the addition funnel until the pH was 2.5–3 (roughly 45 ml). The solution was then purged for two hours with nitrogen while cooling then placed in an ice bath until the slurry was roughly 5° C. The precipitate was isolated by filtration and washed with liberally with water and dried in vacuum. By this method 43.4 g BTA were obtained. Based on $^{13}$C NMR, the BTA product was impure.

EXAMPLE 10

In a 1 liter round bottom flask with magnetic stirrer and reflux condenser were combined 400 ml of water, 37 g of sodium dicyanamide, 99.8 g of sodium bisulfate. The pH was considered too low (roughly 1) to be safe for sodium azide addition, so the experiment was aborted.

EXAMPLE 11

In a 1 liter round bottom flask with magnetic stirrer and reflux condenser were combined 400 ml of water, 70 g of sodium bicarbonate and 54 g sodium azide. After 24 hours reflux, the solution was acidified with hydrochloric acid and poured into 1 liter of water. A small amount of BTA precipitated.

EXAMPLE 12

In a 500 ml round bottom flask with magnetic stirrer and reflux condenser were combined 200 ml of water, 18.5 g of sodium dicyanamide and 27 g of sodium azide. The pH was 10–11. The resulting solution was heated to reflux overnight after which the pH was 10. The resulting solution was acidified with 70 ml hydrochloric acid to achieve pH of 1. The resulting mixture was added to 600 ml of water and cooled with ice. A small amount of BTA precipitated from the solution.

EXAMPLE 13

In a 1 liter round bottom flask with magnetic stirrer and reflux condenser were combined 400 ml of water, 37 g of sodium dicyanamide, 50.7 g boric acid, and 54 g of sodium azide. The pH was 6 upon combining. The mixture was heated to reflux overnight and then acidified with concentrated hydrochloric acid, diluted with 500 ml water to obtain a pH of 1, and cooled to ambient. The solid was collected by filtration, washed with water, and dried under vacuum. By this method, 32.5 g of BTA were obtained.

EXAMPLE 14

In a 12 liter three-necked round bottom flask with an overhead stirrer, reflux condenser, thermometer and nitrogen inlet were combined 4000 ml of water, 1223 g of boric acid, 444 g of sodium dicyanamide and 648 g of sodium azide. The resulting solution was heated to 93°–95° C. for 24 hours. The solution was pumped hot into 4 liters of concentrated hydrochloric acid then cooled by addition of 4 liters of ice. The precipitate was isolated by filtration and washed with liberally with water and dried in vacuum at 60° C. By this method 319 g BTA were obtained.

EXAMPLE 15

In a 1 liter three-necked round bottom flask with an overhead stirrer, reflux condenser, addition funnel, thermometer and nitrogen inlet were combined 400 ml of water, 47 g of ammonium chloride, 37 g of sodium dicyanamide and 52 g of sodium azide. The resulting solution was heated to 92°–95° C. for 24 hours then diluted with 200 ml water. Concentrated hydrochloric acid was added via the addition funnel until the pH was 2.5–3 (roughly 45 ml). The solution was then purged for two hours with nitrogen while cooling and then placed in an ice bath until the slurry was roughly 5° C. The precipitate was isolated by filtration and washed liberally with water and dried in vacuum. By this method, 40 g BTA were obtained. Based on $^{13}$C NMR, the BTA product was impure.

EXAMPLE 16

In a 1 liter three-necked round bottom flask with an overhead stirrer, reflux condenser, addition funnel, thermometer and nitrogen inlet were combined 400 ml of water, 102 g of boric acid, 37 g of sodium dicyanamide and 54 g of sodium azide. The resulting solution was heated to 95° C. for 18 hours at which time the pH of the solution was 8. To the hot solution was added 100 ml of concentrated hydrochloric acid to obtain a pH of 1. During acidification a precipitate formed. The slurry was poured into 2 liters of ice water. The precipitate was isolated by filtration and washed liberally with water and dried in vacuum at 60° C. By this method, 55 g BTA were obtained.

EXAMPLE 17

In a 1 liter three neck round bottom flask equipped with a mechanical stirrer, thermometer and condenser was placed 42.5 g of sodium dicyanamide and 200 ml of distilled water followed by 77.0 g of boric acid. The contents of the flask were then heated to 95° C. and 54.0 g of sodium azide in 200 ml of distilled water added gradually over several hours at a rate of 5.2 ml/minute. The precipitate was isolated by filtration, washed liberally with water, and dried in vacuum. A moderate yield of BTA was obtained.

EXAMPLE 18

In a 1 liter three neck round bottom flask equipped with a mechanical stirrer, thermometer and condenser was placed 44.4 g of sodium dicyanamide and 400 ml of distilled water followed by 54.0 g of sodium azide. The contents of the flask were heated to reflux and boric acid (76.5 g) was added in approximate 20 g portions at such a rate to maintain the pH of 6. Following the addition, the reaction was maintained at reflux for six hours at which time the $^{13}$C NMR indicated that there remained significant starting material, and the reaction product was not further processed.

EXAMPLE 19

In a 1 liter three neck round bottom flask equipped with a mechanical stirrer, thermometer and condenser was placed 76.0 g of boric acid and 44.4 g of sodium dicyanamide in 400 ml of distilled water. The contents of the flask were heated to reflux and small samples were taken each hour for examination by $^{13}$C NMR. The samples collected were evaporated to dryness in a stream of nitrogen and a measured quantity of the residue (0.1700–0.1800 g) was placed in an NMR tube along with 0.0500–0.0550 g of 1,1,2,2-tetrachloroethane as an internal standard. The contents of the tube were then dissolved in 1.00 ml of d6-DMSO and their $^{13}$C NMR spectra recorded on a Varian 300 MHz NMR spectrometer, using a delay time sufficiently long such that all nuclei had relaxed (5 times the measured T1 for sodium dicyanamide, 1.95 seconds). The following data was determined from the integrals of the various samples and indicates a loss of up to 6% of the dicyanamide over a 24 hour period at reflux.

| Hours | Relative Quantity |
|-------|-------------------|
| Start | 0.53 |
| 1     | 0.53 |
| 2     | 0.53 |
| 5     | 0.50 |
| 24    | 0.47 |

EXAMPLE 20

In a 1 liter three neck round bottom flask equipped with a mechanical stirrer, thermometer, and reflux condenser was placed 51.0 g of boric acid, 54.0 g of sodium azide, and 44.4 g of sodium dicyanamide in 400 ml of distilled water. The contents of the flask were heated to 95° C. for 24 hours. To the hot solution was added 125 ml of concentrated HCl. The contents of the flask were then cooled in an ice bath and the resulting thick slurry filtered to collect the precipitated BTA. The solids were washed several times with fresh distilled water until the filtrate had a pH of 3. The solid was then dried in vacuo yielding 31.2 g of clean BTA.

EXAMPLE 21

In a 1 liter three neck round bottom flask equipped with a mechanical stirrer, thermometer, and reflux condenser was placed 51.0 g of boric acid, 54.0 g of sodium azide, and 44.4 g of sodium dicyanamide in 400 ml of distilled water. The contents of the flask were heated to 75° C. for 24 hours. To the hot solution was added 125 ml of concentrated HCl. The contents of the flask were then cooled in an ice bath and the resulting slurry filtered to collect the precipitated BTA. The solids were washed several times with fresh distilled water until the filtrate had a pH of 3. The solid was then dried in vacuo yielding 6.0 g of clean BTA.

EXAMPLE 22

In a 1 liter three neck round bottom flask equipped with a mechanical stirrer, thermometer, and reflux condenser was placed 102.0 g of boric acid, 54.0 g of sodium azide, and 44.4 g of sodium dicyanamide in 400 ml of distilled water. The contents of the flask were heated to 95° C. for 24 hours. To the hot solution was added 125 ml of concentrated HCl. The contents of the flask were then cooled in an ice bath and the resulting slurry filtered to collect the precipitated BTA. The solids were washed several times with fresh distilled water until the filtrate had a pH of 3. The solid was then dried in vacuo yielding 33.9 g of clean BTA.

EXAMPLE 23

In a 1 liter three neck round bottom flask equipped with a mechanical stirrer, thermometer, and reflux condenser was placed 102.0 g of boric acid, 54.0 g of sodium azide, and 40.7 g of sodium dicyanamide in 400 ml of distilled water. The contents of the flask were heated to 95° C. for 24 hours. To the hot solution was added 150 ml of concentrated HCl. The contents of the flask were then cooled in an ice bath and the resulting thick slurry filtered to collect the precipitated BTA. The solids were washed several times with fresh distilled water until the filtrate had a pH of 3. The solid was then dried in vacuo yielding 28.5 g of clean BTA.

EXAMPLE 24

In a 1 liter three neck round bottom flask equipped with a mechanical stirrer, thermometer, and reflux condenser was placed 77.0 g of boric acid, 54.0 g of sodium azide, and 42.5 g of sodium dicyanamide in 400 ml of distilled water. The contents of the flask were heated to reflux for 24 hours. The solution was cooled to room temperature and then pumped in 150 ml of concentrated HCl in 400 ml ice water. The resulting thick slurry was filtered to collect the precipitated BTA. The solids were washed several times with fresh distilled water until the filtrate had a pH of 3. The solid was then dried in vacuo yielding 45.0 g of clean BTA.

EXAMPLE 25

In a 1 liter three neck round bottom flask equipped with a mechanical stirrer, thermometer, and reflux condenser was placed 77.0 g of boric acid, 54.0 g of sodium azide, and 42.5 g of sodium dicyanamide in 400 ml of distilled water. The contents of the flask were heated to reflux for 24 hours. To the hot solution was added 150 ml of concentrated HCl. The contents of the flask were then cooled in an ice bath and the resulting thick slurry filtered to collect the precipitated BTA. The solids were washed several times with fresh distilled water until the filtrate had a pH of 3. The solid was then dried in vacuo yielding 36.4 g of clean BTA.

EXAMPLE 26

Figure 1:
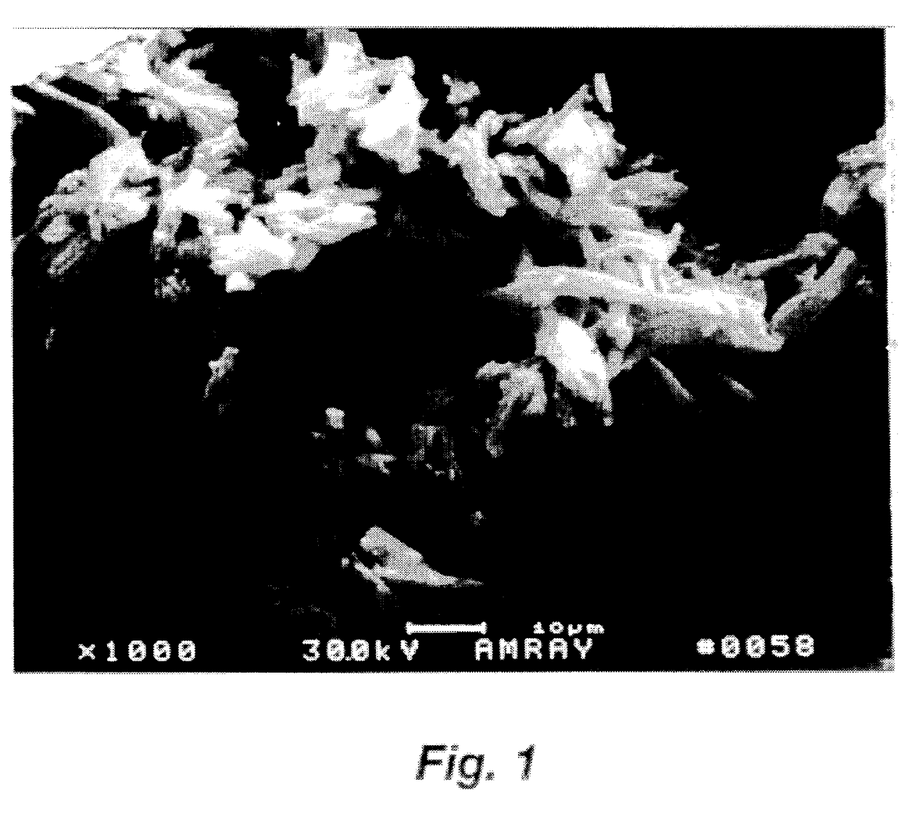
FIG. 1 is photomicrograph at ×1000 magnification showing the highly crystalline, large size of BTA particles prepared according to the procedure of Example 26.
Figure 2:
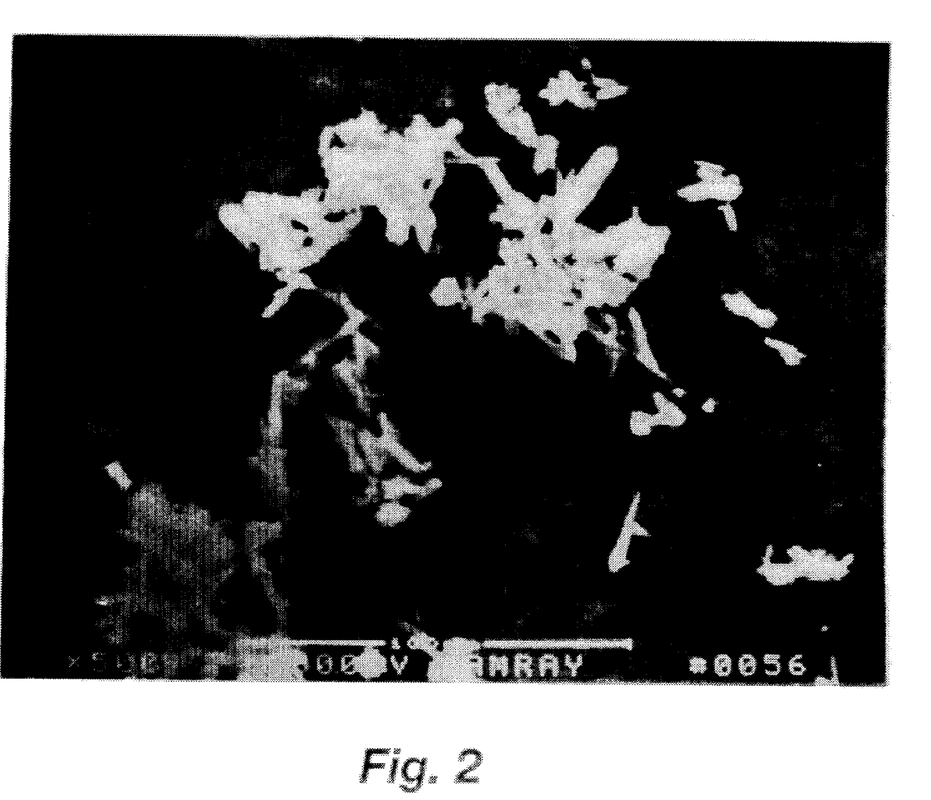
FIG. 2 is photomicrograph at ×500 magnification showing the highly crystalline, large size of BTA particles prepared according to the procedure of Example 26.

In a 22 liter flask equipped with a mechanical stirrer, nitrogen inlets, reflux condensers, and thermometer was placed 1848 g of boric acid and 840 g of sodium dicyanamide in 4.6 liters of distilled water. To this solution was added 1296 g of sodium azide in 4.0 liters of distilled water. The reaction mixture was then refluxed 24 hours at which time a sample was taken, evaporated in a stream of nitrogen, and analyzed by $^{13}C$ NMR. The hot solution was then pumped into a room temperature solution of 2.4 liters of water and 2.4 liters of concentrated HCl. The resulting dark solution was allowed to cool slowly in order to obtain large crystals. After sitting at 5° C. overnight the precipitated BTA was collected by filtration. The solid was then washed by suspension in distilled water, stirring vigorously and subsequently refiltering. This process was repeated until the washings obtained had a pH of 3. The filtercake was then dried in vacuo at 60° C. for several days. The product was obtained (875 g) as a buff white solid which was pure by $^{13}C$ NMR. Photomicrographs were taken of the resulting BTA particles which are presented herein as FIGS. 1 and 2.

EXAMPLE 27

Figure 3:
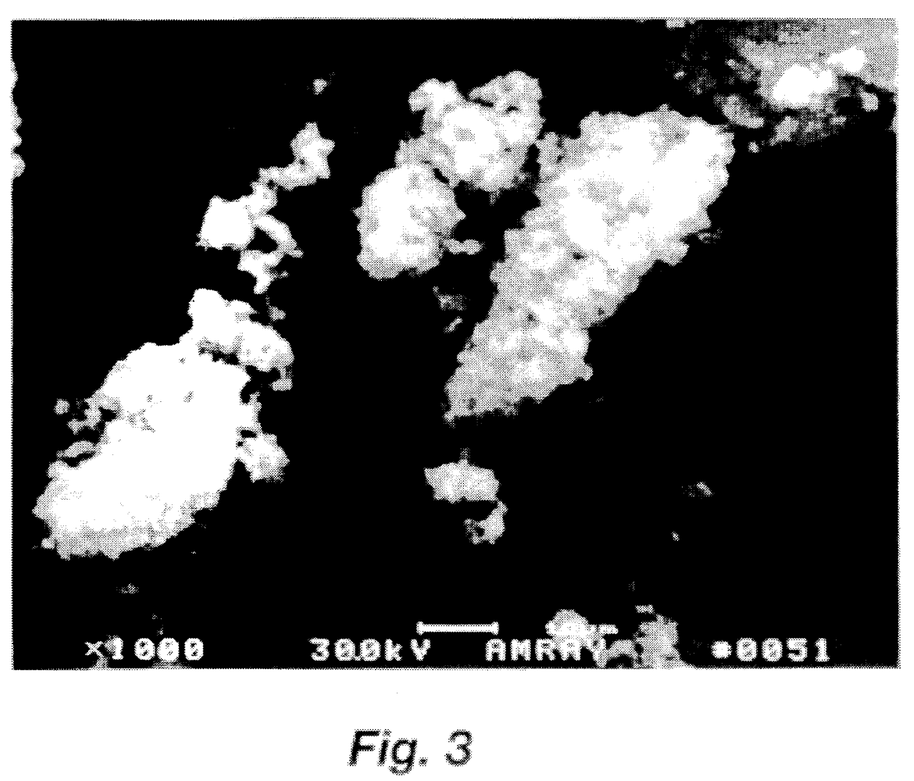
FIG. 3 is photograph at ×1000 magnification showing the amorphous, smaller size BTA particles prepared according to the procedure of Example 27.
Figure 4:
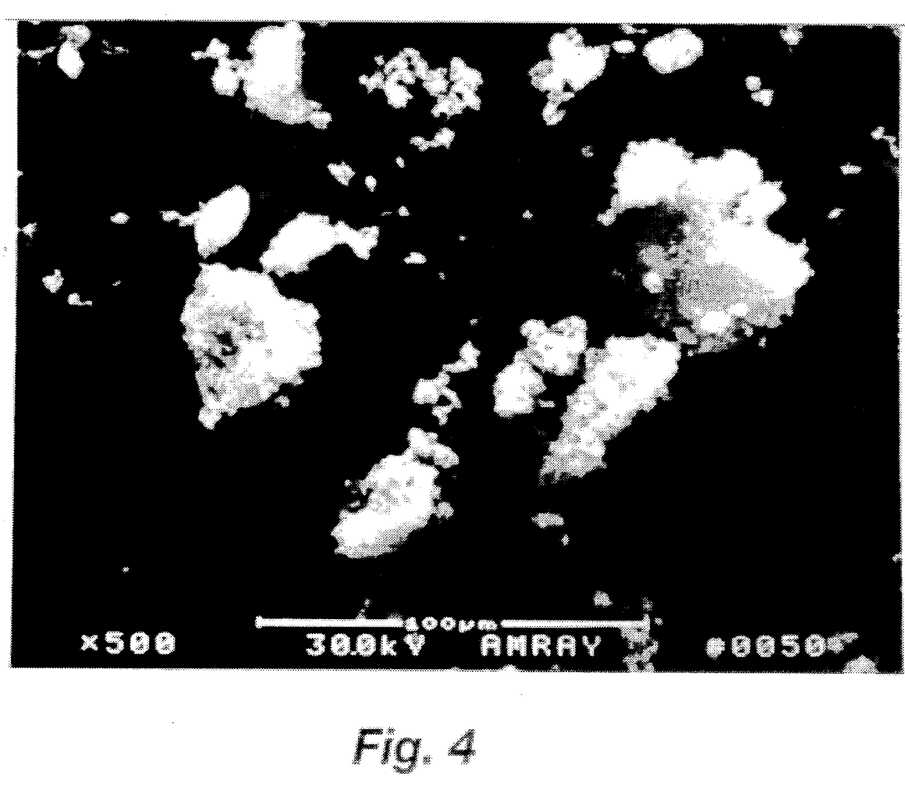
FIG. 4 is photograph at ×500 magnification showing the amorphous, smaller size BTA particles prepared according to the procedure of Example 27.

In a 22 liter flask equipped with a mechanical stirrer, nitrogen inlets, reflux condensers, and thermometer was placed 1848 g of boric acid and 840 g of sodium dicyanamide in 4.6 liters of distilled water. To this solution was added 1296 g of sodium azide in 4.0 liters of distilled water. The reaction mixture was then refluxed 48 hours at which time a sample was taken, evaporated in a stream of nitrogen, and analyzed by $^{13}C$ NMR. The hot solution was then pumped into a 5° C. solution of 2.4 liters of water and 2.4 liters of concentrated HCl. The acidification was not allowed to exceed 15° C. by the addition of ice as necessary to the acid solution. This was done in order to obtain small, amorphous particles. The precipitated BTA was collected by filtration. The solid was then washed by suspension in distilled water, stirring vigorously and subsequently refiltering. This process was repeated until the washings obtained had a pH of 3. The filtercake was then dried in vacuo at 60° C. for several days. The product was obtained (1222 g) as a buff white solid which was pure by $^{13}$C NMR. Photomicrographs were taken of the resulting BTA particles which are presented herein as FIGS. 3 and 4.

Results and experimental conditions for the foregoing examples are summarized below in Table 1.

TABLE 1

| Example | Acid Reagent | Acid/NaN$_3$/DCA (moles) | Temp. | Yield* (%) | Purity |
|---|---|---|---|---|---|
| 1 | NH$_4$Cl | 0.880/0.877/0.416 | reflux | 79.6 | (−)$^a$ |
| 2 | K$_2$HPO$_4$ KH$_2$PO$_4$ | pH 7 buf./0.44/0.202 | reflux | 58.0 | (−)$^b$ |
| 3 | K$_2$HPO$_4$ KH$_2$PO$_4$ | pH 7 buf./0.44/0.202 | reflux | 42.7 | (−)$^b$ |
| 4 | K$_2$HPO$_4$ KH$_2$PO$_4$ | pH 7 buf./1.65/0.800 | reflux | 34.1 | (−)$^b$ |
| 5 | KOAc HOAc | pH 7 buf./0.385/0.202 | reflux | 37.4 | (+) |
| 6 | KOAc HOAc | pH 7 buf./0.420/0.202 | reflux | 35.8 | (+) |
| 7 | KOAc$^\dagger$ HOAc | pH 7 buf./0.420/0.202 | reflux | 35.8 | (−)$^a$ |
| 8 | (CH$_3$)$_2$NH$_2$Cl | 2.08/1.76/0.810 | reflux | wet | (−)$^a$ |
| 9 | NH$_4$Cl | 0.88/0.88/0.416 | 95° C. | 64.5 | (−)$^a$ |
| 10 | NaHSO$_4$ | too acidic (pH 1) | — | aborted | — |
| 11 | NaHCO$_3$ | 0.833/0.831/0.787 | reflux | traces | n/a |
| 12 | none | 0/0.415/0.208 | reflux | traces | n/a |
| 13 | H$_3$BO$_3$ | 0.820/0.83/0.416 | reflux | 51.1 | (+) |
| 14 | H$_3$BO$_3$ | 18.2/9.97/4.94 | reflux | 41.8 | (+) |
| 15 | NH$_4$Cl | 0.880/0.800/0.416 | reflux | 65.4 | (−)$^a$ |
| 16 | H$_3$BO$_3$ | 1.65/0.830/0.416 | 95° C. | 86.5 | (+) |
| 17 | H$_3$BO$_3$ | 1.24/0.83$^\ddagger$/0.480 | reflux | moderate | n/a |
| 18 | H$_3$BO$_3$ | 1.24$^\ddagger$/0.83/0.499 | reflux | moderate | n/a |
| 20 | H$_3$BO$_3$ | 0.825/0.830/0.499 | 95° C. | 49 | (+) |
| 21 | H$_3$BO$_3$ | 0.825/0.830/0.499 | 75° C. | 9.4 | (+) |
| 22 | H$_3$BO$_3$ | 1.68/0.830/0.499 | reflux | 53.5 | (+) |
| 23 | H$_3$BO$_3$ | 1.65/0.830/0.460 | reflux | 44.8 | (+) |
| 24 | H$_3$BO$_3$ | 1.246/0.831/0.478 | reflux | 70.8 | (+) |
| 25 | H$_3$BO$_3$ | 1.246/0.831/0.457 | reflux | 57.2 | (+) |
| 26 | H$_3$BO$_3$ | 29.9/19.9/9.43 | reflux | 57.3 | (+) |
| 27 | H$_3$BO$_3$ | 29.9/19.9/9.43 | reflux | 80.3 | (+) |

DCA = dicyanamide.
*Based on NaN$_3$.
(−) = impure based on $^{13}$C NMR.
(+) = clean based on $^{13}$C NMR.
$^a$Other nitrogenous impurities present.
$^b$Phosphate salts present.
$^\dagger$Slow addition of acid to maintain pH ≈ 7.
$^\ddagger$Portionwise addition.

From the foregoing, it will be appreciated that the present invention provides a process of preparing BTA which uses a readily available, low cost materials and which minimize the formation of hydrazoic acid. The process of preparing BTA according to the present invention also controllably produces small, rounded BTA particles or large, crystalline particles.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The claimed invention is:

1. A process for preparing bis-(1(2)H-tetrazol- 5-yl)-amine comprising the steps of:

(a) combining an azide salt, a dicyanamide salt, and an acid reagent in water, such that at least one mole of the dicyanamide salt is present for every two moles of the azide salt and at least one mole of the acid reagent is present for each mole of the azide salt and wherein the acid reagent has a pK$_a$ in the range from about 3 to about 9, wherein the combined ingredients form a reaction solution;

(b) heating the reaction solution to a temperature greater than 65° C., wherein the combining step occurs either prior to or during said heating step;

(c) acidifying the reaction solution with a strong acid after the reaction is substantially complete to protonate the bis-(1(2)H-tetrazol-5-yl)-amine product; and (d) isolating the bis-(1(2)H-tetrazol-5-yl)-amine product.

2. A process for preparing bis-(1(2)H-tetrazol-5-yl)-amine as defined in claim 1, wherein the reaction solution is heated to reflux temperature.

3. A process for preparing bis-(1(2)H-tetrazol-5-yl)-amine as defined in claim 1, wherein about 1.5 moles of the acid reagent is present for each mole of the azide salt in the reaction solution.

4. A process for preparing bis-(1(2)H-tetrazol-5-yl)-amine as defined in claim 1, wherein the reaction solution is well agitated and wherein the acidifying step is achieved by introducing the strong acid into the reaction solution.

5. A process for preparing bis-(1(2)H-tetrazol-5-yl)-amine as defined in claim 4, wherein the temperature of the reaction solution is greater than 15° C.

6. A process for preparing bis-(1(2)H-tetrazol-5-yl)-amine as defined in claim 4, wherein the reaction solution is at or near reflux temperature.

7. A process for preparing bis-(1(2)H-tetrazol-5-yl)-amine as defined in claim 4, wherein the strong acid is below room temperature.

8. A process for preparing bis-(1(2)H-tetrazol-5-yl)-amine as defined in claim 4, wherein the strong acid has a temperature less than about 15° C.

9. A process for preparing bis-(1(2)H-tetrazol-5-yl)-amine as defined in claim 4, wherein sufficient strong acid is used in the acidifying step to lower the reaction solution's pH to a value of 3 or below.

10. A process for preparing bis-(1(2)H-tetrazol-5-yl)-amine as defined in claim 4, wherein the strong acid is an organic acid having a $pK_a<2$.

11. A process for preparing bis-(1(2)H-tetrazol-5-yl)-amine as defined in claim 4, wherein the strong acid is an inorganic acid having a $pK_a<2$.

12. A process for preparing bis-(1(2)H-tetrazol-5-yl)-amine as defined in claim 4, wherein the strong acid is selected from HCl, $H_2SO_4$, $H_3PO_4$, $HNO_3$, $Cl_2CCO_2H$, $Cl_3CCO_2H$, $F_3CCO_2H$, $HClO_4$, and mixtures thereof.

13. A process for preparing bis-(1(2)H-tetrazol-5-yl)-amine as defined in claim 1, wherein the reaction solution is well agitated and wherein the acidifying step is achieved by introducing the reaction solution into the strong acid.

14. A process for preparing bis-(1(2)H-tetrazol-5-yl)-amine as defined in claim 13, wherein the temperature of the reaction solution during the acidifying step is greater than 15° C.

15. A process for preparing bis-(1(2)H-tetrazol-5-yl)-amine as defined in claim 13, wherein the reaction solution temperature during the acidifying step is at or near reflux temperature.

16. A process for preparing bis-(1(2)H-tetrazol-5-yl)-amine as defined in claim 13, wherein the strong acid is below room temperature.

17. A process for preparing bis-(1(2)H-tetrazol-5-yl)-amine as defined in claim 13, wherein the strong acid has a temperature less than about 15° C.

18. A process for preparing bis-(1(2)H-tetrazol-5-yl)-amine as defined in claim 13, wherein sufficient strong acid is used in the acidifying step to lower the reaction solution's pH to a value of 3 or below.

19. A process for preparing bis-(1(2)H-tetrazol-5-yl)-amine as defined in claim 13, wherein the strong acid is an organic acid having a $pK_a<2$.

20. A process for preparing bis-(1(2)H-tetrazol-5-yl)-amine as defined in claim 13, wherein the strong acid is an inorganic acid having a $pK_a<2$.

21. A process for preparing bis-(1(2)H-tetrazol-5-yl)-amine as defined in claim 13, wherein the strong acid is selected from HCl, $H_2SO_4$, $H_3PO_4$, $HNO_3$, $Cl_2CCO_2H$, $Cl_3CCO_2H$, $F_3CCO_2H$, $HClO_4$, and mixtures thereof.

22. A process for preparing bis-(1(2)H-tetrazol-5-yl)-amine as defined in claim 1, wherein the bis-(1(2)H-tetrazol-5-yl)-amine product is isolated by filtering and washing.

23. A process for preparing bis-(1(2)H-tetrazol-5-yl)-amine as defined in claim 1, wherein the acid reagent has a $pK_a$ in the range from about 3.5 to about 4.5.

24. A process for preparing bis-(1(2)H-tetrazol-5-yl)-amine as defined in claim 1, wherein the acid reagent is boric acid.

25. A process for preparing bis-(1(2)H-tetrazol-5-yl)-amine as defined in claim 1, wherein the acid reagent includes a phosphate buffer.

26. A process for preparing bis-(1(2)H-tetrazol-5-yl)-amine as defined in claim 1, wherein the acid reagent includes an acetate buffer.

27. A process for preparing bis-(1(2)H-tetrazol-5-yl)-amine as defined in claim 1, wherein the acid reagent is ammonium chloride.

28. A process for preparing bis-(1(2)H-tetrazol-5-yl)-amine as defined in claim 1, wherein the azide salt is sodium azide.

29. A process for preparing bis-(1(2)H-tetrazol-5-yl)-amine as defined in claim 1, wherein the dicyanamide salt is selected from the group of Ag, Ca, Cd, Cs, Cu, Fe, K, Mg, Na, and Zn dicyanamide salts, and mixtures thereof.

30. A process for preparing bis-(1(2)H-tetrazol-5-yl)-amine as defined in claim 1, wherein the dicyanamide salt is selected from alkali and alkaline earth dicyanamide salts.

31. A process for preparing bis-(1(2)H-tetrazol-5-yl)-amine as defined in claim 1, wherein the dicyanamide salt is sodium dicyanamide.

32. A process for preparing bis-(1(2)H-tetrazol-5-yl)-amine as defined in claim 1, wherein the azide salt is sodium azide, the dicyanamide salt is sodium dicyanamide, the acid reagent is boric acid, and the strong acid is hydrochloric acid.

33. A process for preparing bis-(1(2)H-tetrazol-5-yl)-amine comprising the steps of:

(a) combining sodium azide, sodium dicyanamide, and boric acid in water, such that at least one mole of the sodium dicyanamide is present for every two moles of the sodium azide and about 1.5 mole of the boric acid is present for each mole of the sodium azide, wherein the combined ingredients form a reaction solution;

(c) heating the reaction solution to about reflux temperature, wherein the combining step occurs either prior to or during said heating step;

(d) acidifying the reaction solution with an acid after the reaction is substantially complete, wherein the reaction solution is well agitated during said acidification step, wherein sufficient acid is used to lower the reaction solution's pH to a value of 3 or below, and wherein the acid is selected from HCl, $H_2SO_4$, $H_3PO_4$, $HNO_3$, $Cl_2CCO_2H$, $Cl_3CCO_2H$, $F_3CCO_2H$, $HClO_4$, and mixtures thereof; and (e) isolating the bis-(1(2)H-tetrazol-5-yl)-amine product.

34. A process for preparing bis-(1(2)H-tetrazol-5-yl)-amine as defined in claim 33, wherein the acidification step is achieved by introducing the acid into the reaction solution.

35. A process for preparing bis-(1(2)H-tetrazol-5-yl)-amine as defined in claim 34, wherein the temperature of the reaction solution is greater than 15° C.

36. A process for preparing bis-(1(2)H-tetrazol-5-yl)-amine as defined in claim 34, wherein the reaction solution is at or near reflux temperature.

37. A process for preparing bis-(1(2)H-tetrazol-5-yl)-amine as defined in claim 34, wherein the acid is below room temperature.

38. A process for preparing bis-(1(2)H-tetrazol-5-yl)-amine as defined in claim 34, wherein the acid has a temperature less than about 15° C.

39. A process for preparing bis-(1(2)H-tetrazol-5-yl)-amine as defined in claim 33, wherein the acidification step is achieved by introducing the reaction solution into acid.

40. A process for preparing bis-(1(2)H-tetrazol-5-yl)-amine as defined in claim 39, wherein the temperature of the reaction solution is greater than 15° C.

41. A process for preparing bis-(1(2)H-tetrazol-5-yl)- amine as defined in claim 39, wherein the reaction solution is at or near reflux temperature.

42. A process for preparing bis-(1(2)H-tetrazol-5-yl)-amine as defined in claim 39, wherein the acid is below room temperature.

43. A process for preparing bis-(1(2)H-tetrazol-5-yl)-amine as defined in claim 39, wherein the acid has a temperature less than about 15° C.

* * * * *